United States Patent
Bhullar et al.

(10) Patent No.: US 6,413,395 B1
(45) Date of Patent: Jul. 2, 2002

(54) BIOSENSOR APPARATUS

(75) Inventors: Raghbir Singh Bhullar, Indianapolis; Jeffery Neal Shelton, Fishers; Brian S. Hill, Indianapolis, all of IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/465,870

(22) Filed: Dec. 16, 1999

(51) Int. Cl.[7] .............................................. G01N 27/327
(52) U.S. Cl. ........................................ 204/403; 204/409
(58) Field of Search .............................. 204/403, 409, 204/400

(56) References Cited

U.S. PATENT DOCUMENTS

| | | | |
|---|---|---|---|
| 4,302,313 A | * | 11/1981 | Columbus .................... 204/403 |
| 4,713,165 A | * | 12/1987 | Conover et al. ............. 204/403 |
| 4,939,563 A | | 7/1990 | Fang et al. |
| 4,963,814 A | | 10/1990 | Parks et al. |
| 4,999,582 A | | 3/1991 | Parks et al. |
| 4,999,632 A | | 3/1991 | Parks |
| 5,051,237 A | * | 9/1991 | Grenner et al. ............. 422/102 |
| 5,243,516 A | | 9/1993 | White |
| 5,312,590 A | * | 5/1994 | Gunasingham ............. 204/403 |
| 5,321,971 A | | 6/1994 | Hobbs et al. |
| 5,330,625 A | * | 7/1994 | Muszak et al. ............. 204/403 |
| 5,352,351 A | | 10/1994 | White et al. |
| 5,366,609 A | | 11/1994 | White et al. |
| 5,385,846 A | | 1/1995 | Kuhn et al. |
| 5,405,511 A | | 4/1995 | White et al. |
| 5,413,690 A | | 5/1995 | Kost et al. |
| 5,438,271 A | | 8/1995 | White et al. |
| 5,496,453 A | | 3/1996 | Uenoyama et al. |
| 5,762,770 A | | 6/1998 | Pritchard et al. |
| 5,837,200 A | | 11/1998 | Diessel et al. |

FOREIGN PATENT DOCUMENTS

| | | |
|---|---|---|
| WO | WO 99/30152 | 6/1999 |
| WO | WO 99/43432 | 9/1999 |

* cited by examiner

Primary Examiner—Robert J. Warden, Sr.
Assistant Examiner—Kaj K. Olsen
(74) Attorney, Agent, or Firm—Jill L. Woodburn

(57) ABSTRACT

According to an aspect of the invention a biosensor apparatus is provided, comprising a base, electrodes positioned on the base, a cover including ports, a plate positioned on the base and including apertures in communication with at least one of the electrodes, a cover including ports in communication with the plate and offset from the apertures, and at least one reagent positioned between the plate and the cover. According to a preferred embodiment the plate includes microstructures extending into the ports of the cover.

35 Claims, 4 Drawing Sheets

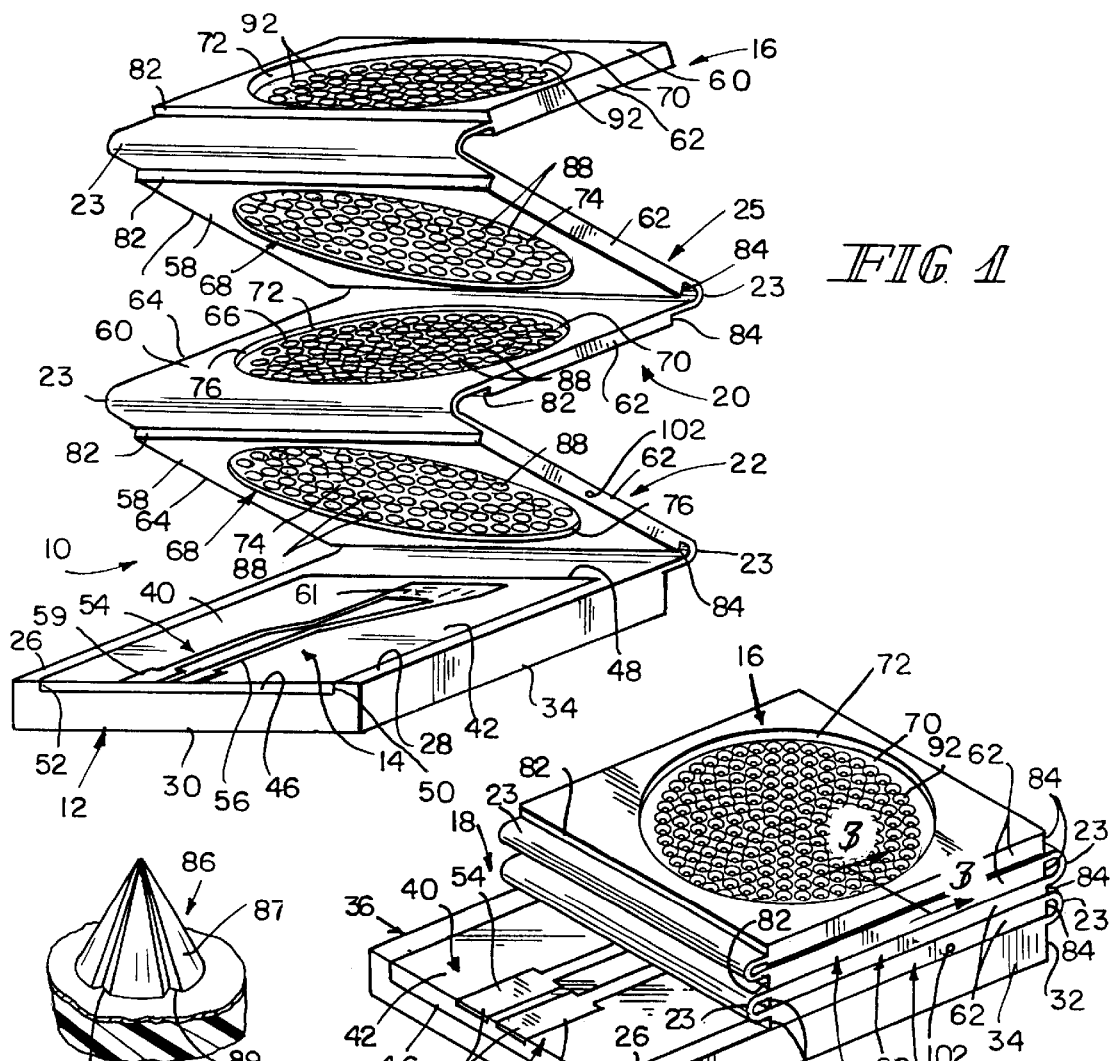
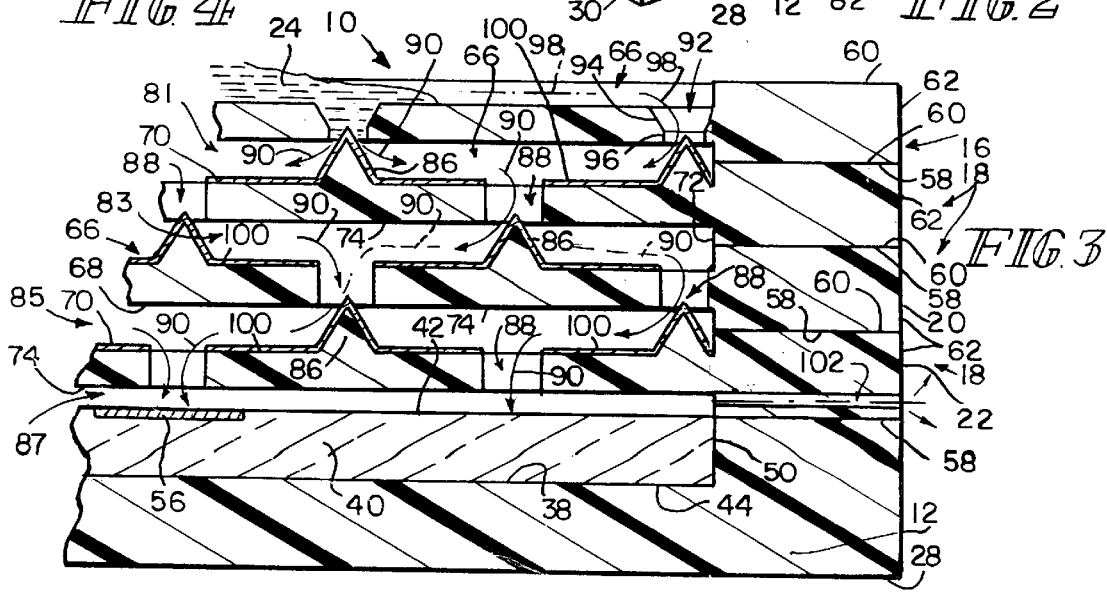

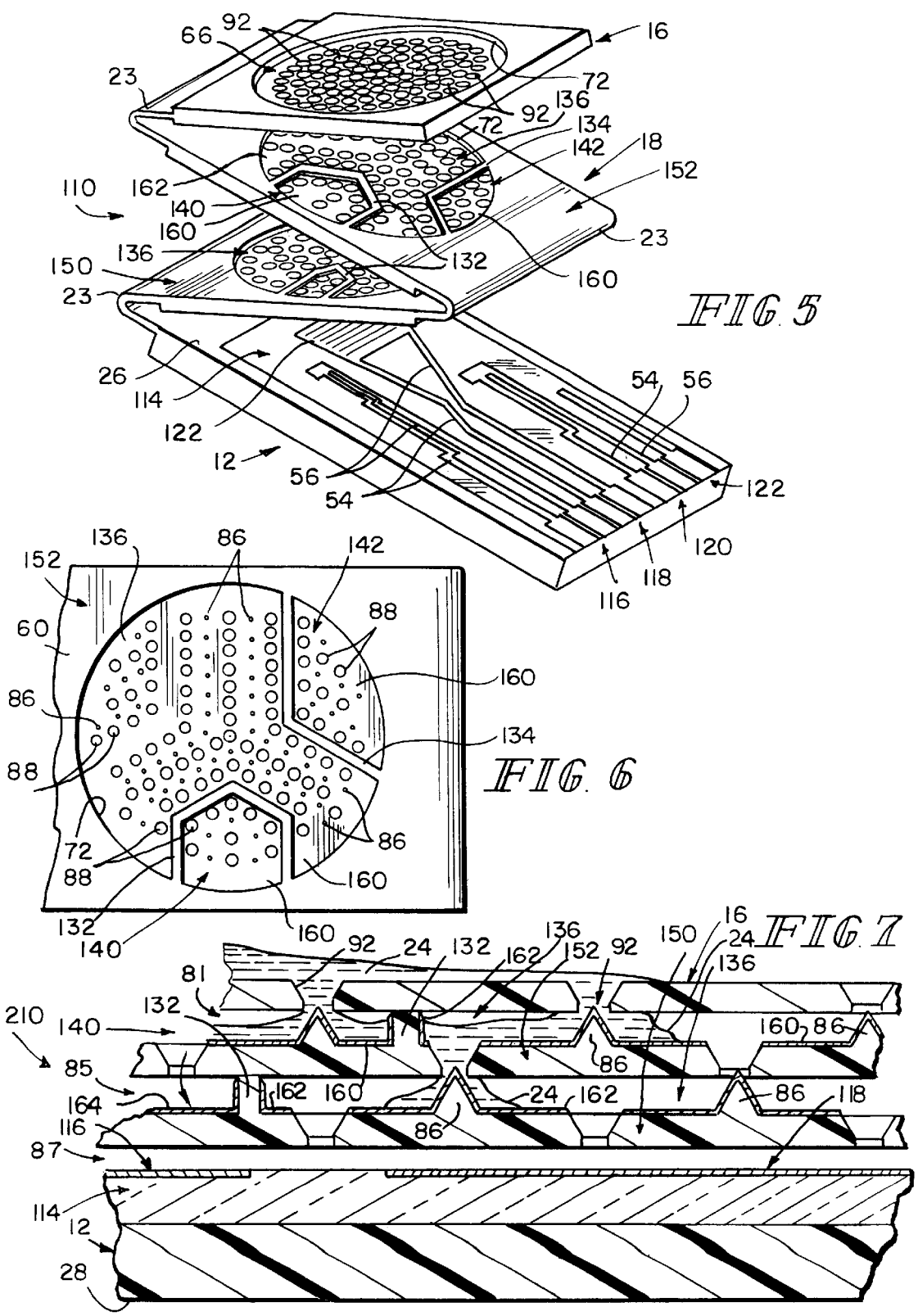

BIOSENSOR APPARATUS

FIELD OF THE INVENTION

The present invention relates to a sensor, more particularly to a top dose sensor.

BACKGROUND OF THE INVENTION

Electrochemical biosensors are known. They have been used to determine the concentration of various analytes from biological samples, particularly from blood. Electrochemical biosensors are described in U.S. Pat. Nos. 5,413,690; 5,762,770; and 5,798,031; as well as in International Publication No. WO99/30152, the disclosure of each of which are hereby incorporated by reference.

SUMMARY OF THE INVENTION

According to the present invention, a biosensor apparatus is provided that comprises a base, electrodes positioned on the base, a cover including ports, at least one plate positioned between the electrodes and the cover, and a reagent situated on at least one plate. At least one plate includes apertures and microstructures spaced-apart from the apertures.

In addition, according to the present invention a biosensor apparatus is provided that comprises a base, electrodes positioned on the base, a plate positioned on the base, a cover, and at least one reagent positioned between the plate and the cover. The plate includes apertures in communication with at least one of the electrodes and the cover includes ports disposed through the cover. The ports are in communication with the plate and offset from the apertures.

Still further, the present invention provides a biosensor apparatus that comprises a base, electrodes positioned on the base, a first plate positioned on the base, a second plate positioned on the first plate, a cover positioned on the second plate, and a reagent positioned on at least one of the first and second plates. The first and second plates each include apertures in an offset relationship relative to one another and the cover includes ports in an offset relationship to the apertures of the second plate.

Additionally, in accordance with the present invention a biosensor apparatus for detecting an analyte in a fluid sample is provided. The biosensor apparatus comprises a base, electrodes positioned on the base, a cover spaced-apart from the electrodes and being formed to include ports sized to receive the fluid sample a reagent, and means for distributing the fluid sample from the ports in the cover to the electrodes. The distributing means is formed to spread the fluid sample radially outwardly from the port in the cover and to also permit the fluid to flow in a direction generally perpendicular to the cover toward the electrodes.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 1 is a perspective view of an electrochemical sensor according to an aspect of the invention in a partially expended position;

FIG. 2 is a perspective view of the sensor of FIG. 1 in a folded position;

FIG. 3 is a view taken along lines 3—3 of FIG. 2;

FIG. 4 is an enlarged perspective view of a microstructure of the sensor of FIG. 3;

FIG. 5 is a perspective view of an electrochemical sensor according to a further aspect of the invention in a partially expanded position;

FIG. 6 is a top plan view of an upper plate of the sensor of FIG. 5;

FIG. 7 is a cross-sectional view of the sensor of FIG. 5 in a folded position;

DETAILED DESCRIPTION OF THE DRAWINGS

Figure 8:
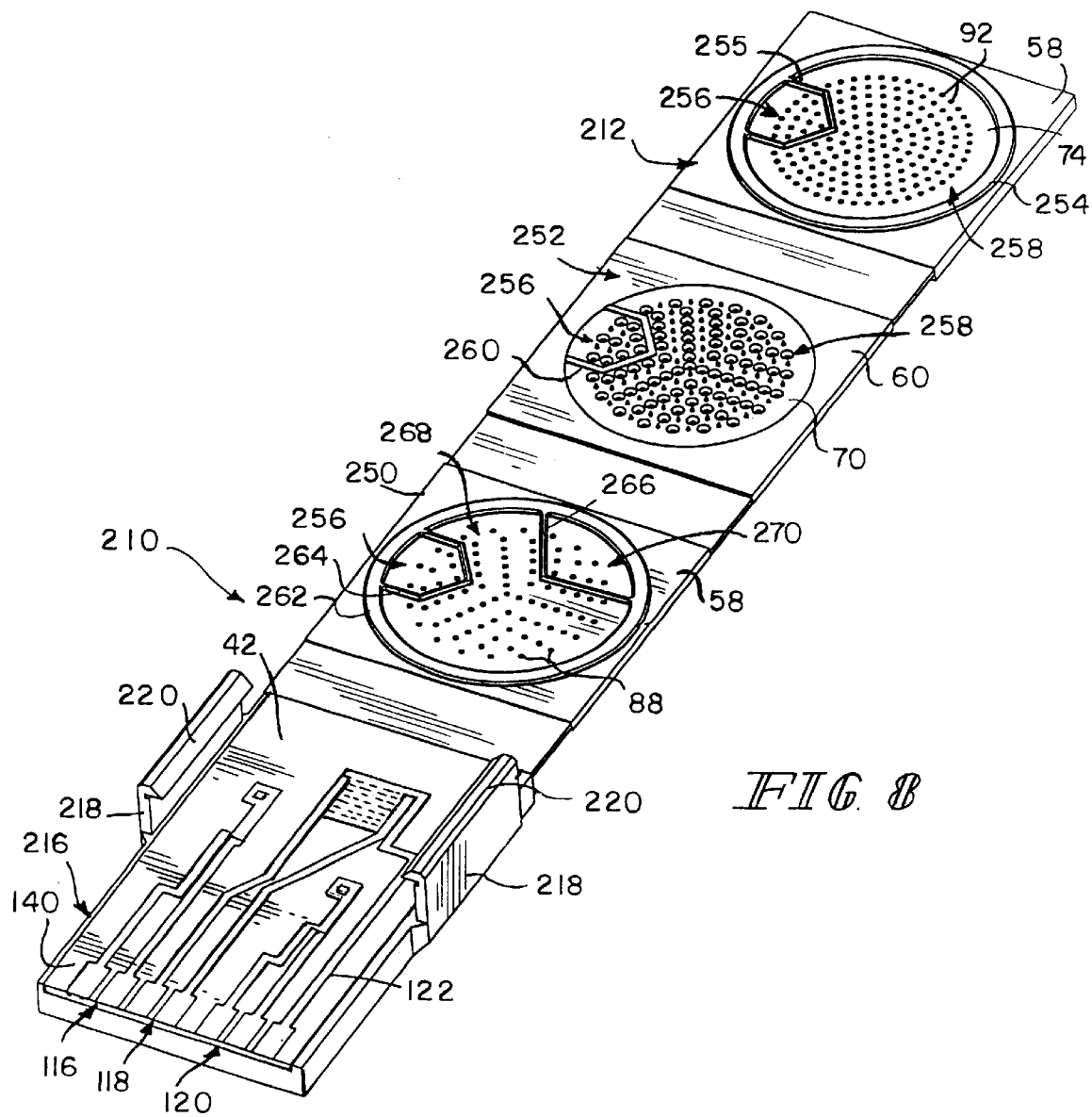
FIG. 8 is a perspective view of an electrochemical sensor according to a further aspect of the invention in a fully expanded position.

The present invention relates to a top dose sensor that provides a manufacturer with the ability to transport a liquid sample both horizontally and vertically in relatively short times. The sensor of the present invention, comprises a series of perforated plates that are formed so that adjacent plates are situated in a generally parallel overlapping relationship to form a fluid distribution gap between the adjacent plates. The apertures of the plates are offset from one another. Thus, the liquid flows through the series of plates, alternating in vertical flow through the apertures and horizontal flow through the fluid distribution gap between the plates.

Various aspects of the invention are presented in FIGS. 1–10, which are not drawn to scale and wherein like components in the several views are numbered alike. Referring now specifically to FIGS. 1–3, a sensor 10 of the present invention includes a base 12, an electrode set 14 positioned on base 12, a cover 16, a series of plates 18, and a series of hinges 23 connecting base 12, cover 16, and series of plates 18 together. Cover 16 and plates 18 cooperate to distribute a liquid sample 24 horizontally as sample 24 travels toward electrode set 14. As will be discussed later in detail, base 12, cover 16, series of plates 18 and hinges 23 are formed from a single piece of molded multi-resinous material.

Electrode set 14 and series of plates 18 are supported on base 12 of sensor 10. Base 12 includes a top surface 26 facing series of plates 18, a bottom surface 28, a front end 30, a back end 32, and side walls 34, 36. A cavity 38 is formed through top surface 26 and front end 30. Cavity 38 is sized to receive an electrical insulator 40 therein. While base 12 is shown to be generally rectangular in shape, it is contemplated that base 12 may be formed in a variety of shapes and sizes in accordance with this disclosure.

As shown in FIGS. 1 and 3, insulator 40 is coupled to base 12 within cavity 38. Insulator 40 includes an upper side 42, a lower side 44 engaging base 12, a front end 46 positioned adjacent to front end 30 of base 12, a back end 48, and sides 50, 52. As shown in FIG. 1, electrode set 14 extends across upper side 42 of insulator 40 from front end 46 toward back end 48. Insulator 40 is formed to prevent an electrical connection from existing between the electrodes of electrode set 14. Non-limiting examples of a suitable insulator 40 include glass, ceramics, and polymers such as a polyester or polyimide. Specific examples of a suitable material include glass; the polyimide UPILEX from UBE INDUSTRIES, LTD., Japan, which is available pre-coated with gold, palladium or platinum from TECHNI-MET of Connecticut, USA; or ULTEM 1000 (polyetherimide) from GE, available coated with copper. Preferably, the insulator is constructed of glass and electrode set 14 is positioned in the glass. Additionally, insulator 40 is coupled to base 12 by an adhesive. It is contemplated, however, that insulator 40 can be coupled to base 12 using solvent-based adhesives, ultrasonic welding, or mechanical fasteners such as dovetails, pins, snaps, rivets, screws, staples, or the like in accordance with this disclosure.

As shown in FIG. 1, electrode set 14 includes two electrically conductive tracks 54, 56 that are laid down into upper side 42 of insulator 40. Track 54 may be a working electrode and track 56 may be a counter electrode. Tracks 54, 56 are constructed from electrically conductive materials. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. Preferably, the tracks include gold, platinum, palladium, iridium, or alloys of these metals, since such noble metals and their alloys are unreactive in biological systems. Most preferably, track 54 is a working electrode made of gold, and track 56 is a counter electrode that is also made of gold and is substantially the same size as the working electrode.

Tracks 54, 56 that serve as working and counter electrodes respectively have contact pads 59 that are electrically connected to a sensing region 61. The values for the dimensions illustrated in FIGS. 1–3 are for a single specific embodiment and these values may be selected as need for the specific use. For example, the length of electrode set 14 may be 1.5 to 250 mm, the width may be 0.4 to 40 mm, the gap between contact pads 59 may be 0.1 $\mu$m to 5 mm, and the width of each contact pad 59 may be 0.1 to 20 mm. The electrode pattern shown in FIG. 1 is symmetric; however this is not required, and irregular or asymmetric patterns (or electrode shapes) are possible. It is also contemplated that electrode set 14 can be coupled to insulator 40 using a wide variety of techniques, such as adhesives, dovetail connections, hook-and-loop type fasteners, etc. in accordance with this disclosure. It is also contemplated that electrodes may be positioned on base 12 using commercially available techniques such as screen printing, sputtering, laser ablation, photolithography, etc. in accordance with this disclosure.

Series of plates 18 extends between base 12 and cover 16 and distributes sample 24 in a horizontal direction as sample 24 travels from cover 16 toward electrode set 14. Series 18 includes a first plate 22 resting upon base 12, a second plate 20 resting upon first plate 22, and a third plate 25 adjacent to cover 16 and resting upon second plate 20. See FIG. 2. It is contemplated that series 18 may have as few as one or two plates or may have greater than three plates. Series of plates 18 are coupled together so that plates 20, 22, 25 are positioned in a generally parallel relationship relative to one another when in a folded position, as shown in FIG. 2.

Each plate 20, 22, 25 in series 18 includes an inner side 58 and an outer side 60. As shown in FIGS. 2 and 3, plates 20, 22, 25 are positioned with respect to base 12 so that outer side 60 of each lower plate in series 18 supports inner side 58 of an adjacent upper plate in series 18. Referring now to FIG. 3, outer side 60 of each plate 20, 22, 25 includes an upper recess 66 that is defined by an upper face 70 and a wall 72 extending from upper face 70. Likewise, inner side 58 of plates 20, 22, 25 includes a lower recess 68 defined by a lower face 74 and a wall 76 extending from lower face 74. Walls 72, 76 are in general alignment with one another to limit the amount of horizontal distribution of sample 24 on plates 20, 22, 25. Upper face 70 of each plate 20, 22, 25 is preferably hydrophilic to aid in the distribution of sample 24. While upper and lower faces 70, 74 each have a generally circular shape (FIG. 1), it is contemplated that faces may be oblong, triangular, square, rectangular, trapezoidal, etc. in shaped in accordance with this disclosure.

When sensor 10 is in the folded position, as shown in FIGS. 2 and 3, plates 20, 22, 25 are stacked on top of one another. Lower recess 68 of cover 16 and upper recess 66 of plate 25 cooperate to define a first horizontal distribution gap 81. Lower recess of plate 25 and upper recess of plate 20 cooperate to define a second horizontal distribution gap 83. Likewise, lower recess 68 of plate 20 and upper recess 66 of plate cooperate to define a third horizontal distribution gap 85 and lower recess 68 of plate 22 and insulator 40 cooperate to define a fourth horizontal distribution gap 87. Distribution gaps 81, 83, 85, 87 are generally perpendicular to apertures 88 in plates in series 18. In addition plate 22 includes an air vent 102 that extends between lower recess 68 and an edge 62 of plate 22. It is contemplated that vent 102 may have a variety of sizes and paths and may extend through any one or greater than one of the plates 22, 20, 25 or from upper recess 66 in accordance with this disclosure, so long as air is vented from sensor 10 as sample 24 travels toward electrode set 14.

Sensor 10 of the present invention pulls sample 24 from cover 16 toward electrode set 14. This movement is accomplished both by gravity and by increasing capillary pull as sample 24 moves from cover 16 toward electrode set 14. The capillary strength of series of plates 18 increases from cover 16 to insulator 40 as the height of distribution gaps 81, 83, 85, 87 decreases. Horizontal distribution gaps 81, 83, 85, 87 range in height from about 5 $\mu$m to 1000 $\mu$m, preferably about 10 $\mu$m to 200 $\mu$m, and most preferably about 25 $\mu$m to 100 $\mu$m. For example, first distribution gap 81 has a height of about 100 $\mu$m, second distribution gap 83 has a height of about 75 $\mu$m, third distribution gap 85 has a height of about 50 $\mu$m, and fourth distribution gap 87 has a height of about 25 $\mu$m. It is contemplated that the height of distribution gaps 81, 83, 85, 87 may be substantially equal, or may vary so long as height of gap 81, 83, 85, 87 is sufficient to pull sample 24 across the corresponding plate 25, 20, 22 or insulator 40 by capillary action.

As shown in FIG. 3, each plate 20, 22, 25 includes microstructures 86 extending from upper face 70 into recess 66 and apertures 88 extending through upper and lower faces 70, 74. Referring now to FIG. 4, microstructures 86 are cone-shaped and are formed to include an interrupted face 87 suitable for providing an edge for sample 24 and make a smooth transition between plates 20, 22, 25. Interrupted face 87 of microstructures is defined by four V-shaped grooves 89 positioned in spaced-apart relation to one another. It is contemplated that grooves may vary in number and positioning about the surface of interrupted face 87 and that microstructures may be formed with a smooth face in accordance with this disclosure. In addition, it is contemplated that microstructures may be formed to include platforms that protrude from interrupted face 87.

Microstructures 86 also guide movement of sample 24 in a generally horizontal direction in gaps 81, 83, 85 as shown by arrows 90 in FIG. 3. Microstructures 86 are aligned with apertures 88 in the vertically elevated plate in series 18.

Microstructures 86 extend through an opening of aperture 88 in adjacent plate in series 18. It is contemplated that microstructures 86 may have a variety of heights and angles and may be formed as cylinders, bumps, triangles, pyramids, blocks, etc. in accordance with the present disclosure. It is also contemplated that apertures 88 may take on a variety of shapes and sizes through plates 20, 22, and 25. Moreover, plates 20, 22, 25 may include greater or fewer than the illustrated microstructures and apertures and plates 20, 22, 25 may be formed to include microstructures and apertures in a variety of patterns in accordance with this disclosure.

Each illustrative plate 20, 22, 25 includes opposite ends 82, 84 and edges 62, 64 that extend across the length of each plate 20, 22, 25 between opposite ends 82, 84. As shown in FIG. 1, plates 20, 22, 25 in series 18 are coupled together at each opposite end 82, 84, which allows series 18 to be situated in an expanded position during manufacture. Hinges 23 extend between base 12 and second end 84 of plate 22, between first ends 82 of plates 20, 22 and second ends 84 of plates 20, 25 respectively, and between first end 82 of plate 25 and cover 16. While hinges 23 are illustrated, it will be contemplated that straps, cords, adhesives, snaps, rods, pins, staples, and the like may be used to couple adjacent plates 20, 22, 25 together.

As shown in FIG. 3, cover 16 of sensor 10 directs the flow of sample 24 toward series of plates 18. Upper face 70 of cover 16 is formed to receive a user's finger thereon to deposit sample 24. In addition, cover 16 includes ports 92 extending through upper and lower faces 70, 74. A tapered portion 94 and a generally cylindrical portion 96 define each port 92. It is contemplated, however, that ports 92 may take on a variety of shapes and sizes through cover 16. Ports 92 are generally aligned with microstructures 86 of third plate 25 and are spaced apart from apertures 88. It is contemplated that while FIG. 2 illustrates cover 16 with ports in a circular pattern, it is contemplated that cover may include greater or fewer than the illustrated ports, ports may be positioned in a variety of patterns through cover 16, and ports may vary in diameter in accordance with this disclosure.

Reagent 100 provides electrochemical probes for specific analytes. The choice of specific reagent 100 depends on the specific analyte or analytes to be measured, and are well known to those of ordinary skill in the art. An example of a reagent that may be used in sensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilodaltons), 3.3 mg NATROSOL 250M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in WO 99/30152, the disclosure of which is incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight:volume) Avicel. A further description of the reagent for a hematocrit assay is found in U.S. Pat. No. 5,385,846, the disclosure of which is incorporated herein by reference.

Other non-limiting examples of enzymes and mediators that may be used in measuring particular analytes in sensor 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate | Diaphorase | Ferricyanide | Phenazine Ethosulfate, or |

TABLE 1-continued

| Analyte | Enzymes | Mediator (Oxidized Form) | Additional Mediator |
| --- | --- | --- | --- |
| Dehydrogenase | | | Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of sample 24 may be accurately correlated to the concentration of the analyte in sample 24 with sensor 10 in accordance with this disclosure.

Sensor 10 is manufactured by multi-resin injection molding. Such a molding process is commercially available from H. Weidmann AG, Neue Jonastrasse 60, CH-8640 Rapperswil, Switzerland. Multi-resin injection molding requires that a suitable multi-resinous material be selected to impart desired characteristics to base 12, plates 20, 22, 25, hinges 23, and cover 16. The multi-resinous material enables base, 12, plates 20, 22, 25, hinges 23, and cover 16 each have an individualized stiffness. Although sensor 10 is preferably manufactured using multi-resin injection molding, it is contemplated that cover 16, series of plates 18, and base 12 may be formed separately and coupled together without exceeding the scope of this disclosure.

Sensor 10 is constructed from a thermoplastic polymeric material, for example acrylonitrile butadiene styrene (ABS), acetal, acrylic, polycarbonate (PC), polyester, polyethylene, fluoroplastic, polyimide, nylon, polyphenylene oxide, polypropylene (PP), polystyrene, polysulfone, polyvinyl chloride, poly (methacrylate), poly (methyl methacrylate), or mixture or copolymers thereof. More preferably, base 12, plates 18, and cover 16 are formed from a polycarbonate, such as those used in making compact discs and hinges 23 are constructed of a thermoplastic rubber (TPR). Specific examples of polycarbonates include MAKROLON™ 2400 from Bayer AG of Leverkusen, Germany; and NOVAREX™ 7020 HF, from Mitsubishi Engineering-Plastics Corporation of Tokyo, Japan. Non-limiting examples of TPR include a polyolefin such as a polypropylene or polyethylene. Specifically, the TPR is Cawiton commercially available from Shell Chemical. The material injection molded to form base 12, series of plates 18, hinges 23, and cover 16, is either a thermoplastic polymeric material, or components that will react to form the material of the thermoplastic polymeric material, such as monomers or polymeric precursors.

The starting reagents are the reactants or components of reagent 100, and are often compounded together in liquid form before application to upper face 70 of each plate 20, 22, 25 when sensor is in the expanded position. Referring now to FIG. 3, the liquid is then evaporated, leaving reagent 100 in solid form coating upper face 70 and microstructures 86 in upper recess 66. While a single reagent 100 may be coated on upper face 70 of each plate 20, 22, 25, it is contemplated that reagent 100 may be separated into different components in accordance with this disclosure. For example, a first enzyme may be situated on first plate 25, a second enzyme situated on second plate 20, and a mediator may be positioned on third plate 22.

A chemical adhesive is applied to inner side 58 of plates 22, 20, 25 and cover 16. Cover 16 and plates 20, 22, 25 are then folded upon one another until sensor 10 is in the folded position of FIG. 2. It is contemplated that sensor 10 can alternatively be bonded together by diffusion or anodic bonding, ultrasonic welding, laser welding, solvent-based adhesives, or mechanically held in the folded position with fasteners, dovetails, pins, snaps, rivets, screws, staples, or the like. When a mechanical connection is utilized, it is beneficial to position a seal such as a gasket between each of the plates 20, 22, 25 to block the flow of sample and reagent from sensor 10.

In use, liquid sample 24 is deposited in upper recess 66 of cover 16. Sample 24 flows into ports 92, as shown by arrow of 98 in FIG. 3. While traveling through ports 92, sample 24 engages reagent-coated microstructures 86, which guide the flow of sample 24 horizontally into first distribution gap 81. Sample 24 dissolves reagent 100 as sample 24 flows across microstructures 86 and along upper face 70 of plate 25 by capillary action, as shown by arrow 90. Sample 24 is pulled by capillary action across plate 25 until sample 24 encounters apertures 88 in plate 25. Sample 24 then flows vertically through aperture 88 and into engagement with corresponding reagent-coated microstructure 86 of second plate 20.

Second distribution gap 83 creates a stronger capillary pull than first distribution gap 81 to pull sample 24 from apertures 88 in plate 25 across plate 20. Microstructures 86 of plate 20 extend into apertures 88 of plate 25 and guide the flow of sample 24 in a generally horizontal direction. See FIG. 3. As sample 24 is pulled along plate 20, reagent 100 that coats microstructures 86 and surface 70 of plate 20 is dissolved. Sample 24 continues its travel across plate 20 until sample 24 encounters apertures 88 in plate 20. Sample then flows vertically through aperture 88 and into engagement with corresponding reagent-coated microstructure 86 of first plate 22.

Third distribution gap 85 creates a stronger capillary pull than second distribution gap 83 to pull sample 24 across plate 22. Microstructures 86 of plate 22 extend into apertures 88 of plate 22 and guide the flow of sample 24 in a generally horizontal direction. See FIG. 3. As sample is pulled along plate 22, reagent 100 that coats microstructures 86 and surface 70 of plate 22 is dissolved. Sample 24 continues its travel across plate 22 until sample 24 encounters apertures 88 in plate 22. Again, fourth distribution gap 87 creates a stronger capillary pull than third distribution gap 85 and pulls sample 24 from apertures 88 in plate 22 and across electrode set 14.

When sample 24 containing the analyte dissolves reagent 100 on plates 20, 22, 25, the analyte is oxidized and the oxidized form of the mediator is reduced. The reaction between the analyte and reagent 100 is permitted to go to completion. (Completion is defined as sufficient reaction involving analyte, enzyme, and mediator (oxidized form) to correlate analyte concentration to diffusion limited current generated by oxidation of the reduced form of the mediator at the surface of the working electrode.) After reaction is complete, a power source (e.g., a battery) applies a potential difference between electrodes. When the potential difference is applied, the amount of oxidized form of the mediator at the counter electrode and the potential difference must be sufficient to cause diffusion-limited electrooxidation of the reduced form of the mediator at the surface of the working electrode. A current measuring meter (not shown) measures the diffusion-limited current generated by the oxidation of the reduced form of the mediator at the surface of the working electrode. The measured current may be accurately correlated to the concentration of the analyte in sample 24 when the following requirements are satisfied:

1. The rate of oxidation of the reduced form of the mediator is governed by the rate of diffusion of the reduced form of the mediator to the surface of the working electrode.

2. The current produced is limited by the oxidation of reduced form of the mediator at the surface of the working electrode.

Sensor 10 of the present invention satisfies the above requirements by employing reagent 100 that includes a readily reversible mediator and by supplying reagent with the oxidized form of the mediator in an amount sufficient to insure that the current produced during diffusion limited electro-oxidation is limited by the oxidation of the reduced form of the mediator at the surface of the working electrode. For current produced during electro-oxidation to be limited by the oxidation of the reduced form of the mediator at the surface of the working electrode, the amount of the oxidized form of the mediator at the surface of the counter electrode must always exceed the amount of the reduced form at the surface of the working electrode.

Sensor 10 is used in conjunction with the following:

1. a power source in electrical connection with the working and counter electrodes and capable of supplying an electrical potential difference between the working and counter electrodes sufficient to cause diffusion limited electro-oxidation of the reduced form of the mediator at the surface of the working electrode; and 2. a meter in electrical connection with the working and counter electrodes and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby incorporated by reference.

Sensor 10 of the present invention may be used to determine the concentration of an analyte in a fluid sample by performing the following steps:

a. placing a fluid sample on upper face 70 of cover 16;

b. allowing the sample to travel through series of plates 18, whereby the sample contacts reagent 100 and permits the reaction between the analyte and the oxidized form of the mediator to go to completion, as defined herein;

c. subsequently applying a direct potential difference between the electrodes sufficient to cause diffusion limited electro-oxidation of the reduced form of the mediator at the surface of the working electrode;

d. thereafter measuring the resulting diffusion limited current; and e. correlating the current measurement to the concentration of analyte in the sample.

Many fluid samples may be analyzed. For example, human body fluids such as whole blood, blood serum, urine, and cerebrospinal fluid may be measured. Also foods, fermentation products and in environmental substances, which potentially contain environmental contaminants, may be measured.

Referring now to FIG. 5, a sensor 110 is provided in accordance with the present invention that provides a manufacturer with the ability to transport a liquid sample both horizontally and vertically in relatively short times. Sensor 110 also enables the user to conduct multiple assays with a single sample by separating the sample into discrete chambers for contact with different reagents and separate electrode sets. For example, sensor 110 may be used to measure glucose and hematocrit concentrations and to measure blank current. Base 12 of sensor 110 receives an insulator 114 that supports three sets of electrodes 116, 118, 120 and a reference electrode 122 that corresponds to electrode set 118. Each electrode set 116, 118, 120 includes two electrically conductive tracks 54, 56 that correspond to a working and counter electrode respectively.

Series of plates 18, shown in FIG. 5, includes a first plate 150 extending from base 12 and a second plate 152 extending between first plate 150 and cover 16. It is contemplated that the series of plates of may have as few as one plate or may have greater than two plates in accordance with this disclosure. Plates 150, 152 are positioned so that they are stacked in a generally parallel relationship relative to one another when sensor 110 is in a folded position as shown in FIG. 7.

Referring now to FIGS. 5 and 6, plates 150, 152 are formed similarly to plates 20, 22 except that upper face 70 of plates 150, 152 includes partitions 132, 134 that cooperate with wall 72 to separate recesses 66, 68 into three distinct regions 136, 140, 142. Partitions 132, 134 extend from face 70 and through recesses 66, 68 to a height sufficient to engage lower face 70 of vertically elevated plate in series 18. Thus, when sensor 110 is in the folded position, (FIG. 7) partitions 132, 134 of plate 150 engage plate 152 and partitions 132, 134 of plate 152 engage cover 16 to limit the amount of horizontal distribution of sample on plate 150, 152. While regions 136, 140, 142 are illustrated in FIG. 6 in a specific pattern, this is not required, and symmetric, irregular or asymmetric patterns are possible in accordance with this disclosure. Moreover, it is contemplated that greater or fewer than three regions may be formed on each plate 150, 152.

Regions 136, 140, 142 cooperate with electrode sets 118, 116, and 120 respectively to enable the user to conduct multiple assays. For example, a glucose assay is conducted by partitioning a portion of sample 24 into region 136 for contact with electrode set 118, and reference electrode 122. A hematocrit assay is conducted by partitioning a portion of sample 24 into region 140 for contact with electrode set 116. Additionally, blank current is measured partitioning a portion of sample 24 into region 142 for contact with electrode set 120. It is contemplated that a variety of assays including those described in Table 1 can be used with sensor 110 of the present invention. Additionally, sensor 110 can be used to measure temperature of sample by partitioning a portion of sample 24 into a region for contact with a thermistor (not shown).

Sensor 110 is constructed in a similar manner to sensor 10 using a multi-resin injection molding. Sensor 110 is also constructed from a thermoplastic polymeric material as discussed above with reference to sensor 10. Preferably, base 12, plates 150, 152, and cover 16 are formed from a polycarbonate, hinges 23 are constructed of a thermoplastic rubber, and partitions are formed from a TPR. When glucose, hematocrit, and blank current are to be measures, a common mediator 160, such as ferricyanide, is applied in liquid form to plate 152 in each region 136, 140, 142. Discrete enzymes are applied in liquid form to plate 152 in regions 136, 140 respectively. The liquid is then evaporated, leaving the reagents in solid form coating upper face 70 and microstructures 86. The choice of specific reagents depends on the specific analytes to be measured, and are well known to those of ordinary skill in the art.

In use, liquid sample 24 is deposited in upper recess 66 of cover 16. Sample 24 flows into ports 92, as shown in FIG. 7. While traveling through ports 92, sample 24 engages reagent-coated microstructures 86, which guide the flow of sample 24 horizontally into first distribution gap 81 in regions 136, 140, 142. Sample 24 dissolves mediator 160 as sample 24 flows across microstructures 86 and along upper face 70 of plate 152 by capillary action, as shown by arrow 90. Partitions 132, 134 limit the amount of horizontal flow of sample 24 across plate 150. Sample 24 is pulled by capillary action across plate 152 in region 136, 140, 142 until sample 24 encounters apertures 88 in plate 152. Sample 24 then flows vertically through aperture 88 and into engagement with reagent-coated microstructure 86 of plate 150 in a corresponding region 136, 140, 142.

Second distribution gap 83 creates a stronger capillary pull than first distribution gap 81 to pull sample 24 across plate 150. Microstructures 86 of plate 20 extend into apertures 88 of plate 152 and guide the flow of sample 24 in a generally horizontal direction. See FIG. 3. As sample 24 is pulled along plate 150, enzymes 162, 164 that coat microstructures 86 and surface 70 of plate 150 in regions 136, 140 are dissolved. Sample 24 continues its travel across plate 20 until sample 24 engages partition 142, 134 or encounters apertures 88 in plate 150. When sample 24 encounters apertures 88, sample 24 flows vertically through aperture 88 toward electrode set 116, 118, 120 that corresponds with region 136, 138, 142 from which sample is flowing.

When sample 24 containing the analyte dissolves reagents on plates 152, 150 the analyte is oxidized and the oxidized form of the mediator is reduced. For current measurement, the reaction between the analyte and reagent 100 is permitted to go to completion and a power source (e.g., a battery) applies a potential difference between electrodes of sets 116, 118. A current measuring meter (not shown) measures the diffusion-limited current generated by the oxidation of the reduced form of the mediator at the surface of the working electrode. A potential difference is also applied between electrodes of set 120 to measure the diffusion-limited current generated by the oxidation of the reduced form of the mediator at the surface of the working electrode in the absence of enzyme, e.g. the blank current. The effects of blank current of the system is therefore accounted for and the measured current of the glucose and hematocrit assays can be used to accurately correlated to the concentration of the analyte in sample as discussed above with reference to sensor 10.

Figure 9:
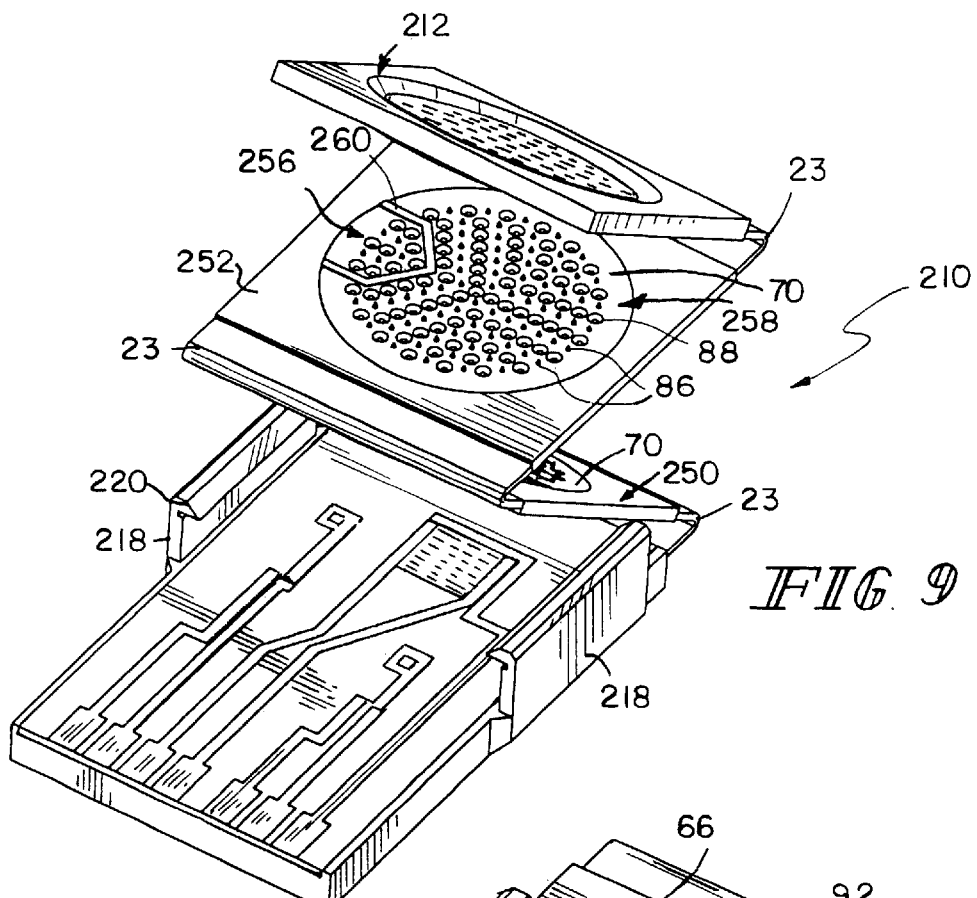
FIG. 9 is a perspective view of the sensor of FIG. 8 is a partially expanded position.
Figure 10:
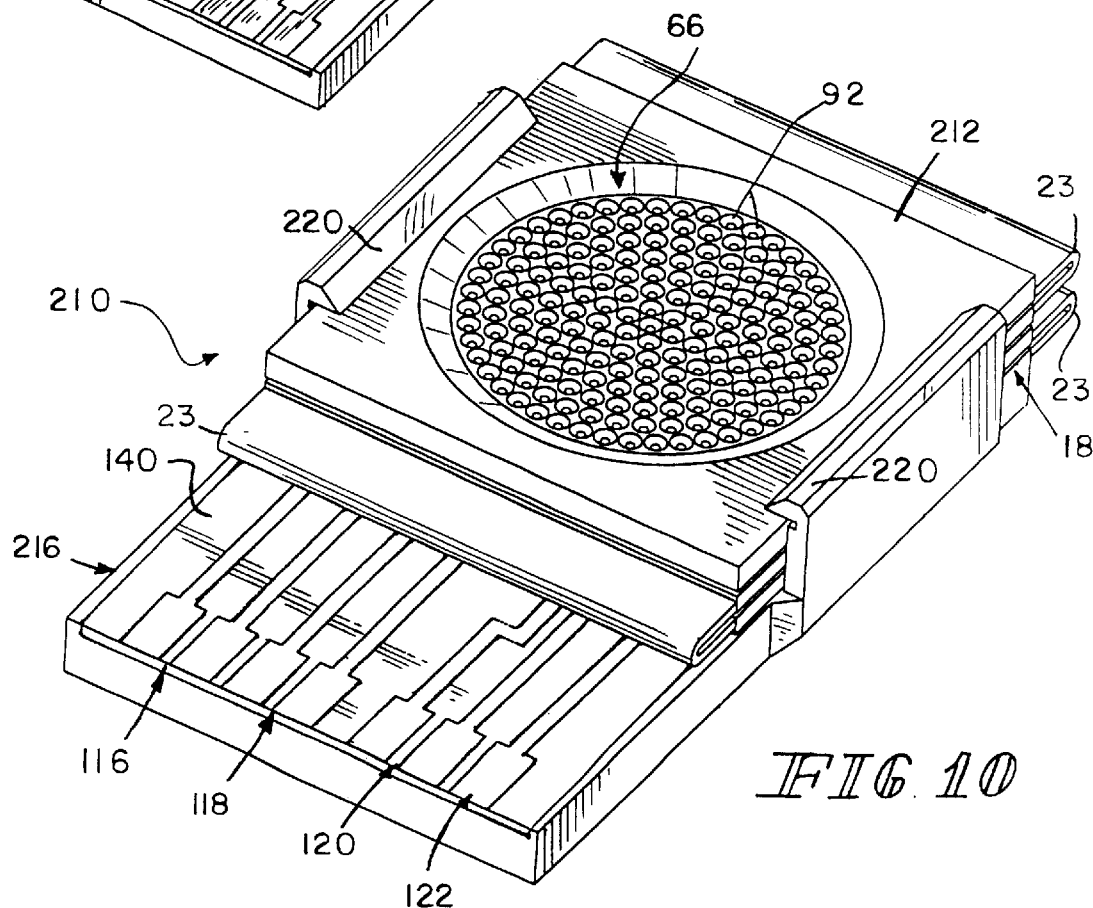
FIG. 10 is a perspective view of the sensor of FIG. 8 in a folded position.

Referring now to FIGS. 8–10, a sensor 210 is provided in accordance with the present invention that provides a manufacturer with the ability to transport a liquid sample both horizontally and vertically in relatively short times. Sensor 210 also enables the user to conduct multiple assays with a single sample by separating the sample into discrete chambers for contact with different reagents and separate electrode sets. For example, sensor 210 may be used to measure glucose, hematocrit, and a blank current.

Sensor 210 includes base 216 that supports insulator 140. Base 216 includes side panels 218 extending from side walls 34, 36. Each panel 218 includes a tab 220 that is formed to hold cover 212 and series of plates 18 securely on base 216. Series of plates 18 shown in FIGS. 8 and 9 includes a first plate 250 extending from base 12 and a second plate 252 extending between first plate 250 and cover 16. It is contemplated that the series of plates of may have as few as one plate or may have greater than two plates in accordance with this disclosure. Plates 250, 252 are positioned so that they are stacked in a generally parallel relationship relative to one another when sensor 210 is in a folded position as shown in FIG. 10.

Referring now to FIG. 8, cover 212 is similar to cover 16, except that cover 212 includes a seal 254 that extends about the periphery of lower face 74. Seal 254 also includes an inner portion 255 that extends across face 74 to form two distinct regions 256, 258. When sensor 210 is in the folded position of FIG. 10, seal 254 engages outer side 60 of plate 252 to form a sealing engagement between cover 212 and plate 252. Seal 254 is preferably constructed of the TPR as previously discussed.

As shown in FIG. 8, plates 250, 252 are formed similarly to cover 16 and plates 20, 22, except that upper face 70 of plate 252 includes a partition 260 that lies in general alignment with inner portion 255 of seal 254. Partition 260 divides upper face into regions 256, 258. In addition, plates 250, 252 include a seal 262 that extends about the periphery of lower face 74. Seal 262 also includes first and second inner portions 264, 266 that extends across face 74 to form three distinct regions 256, 268, 270. Seals 262 are preferably constructed of the TPR as previously discussed.

When sensor 210 is in the folded position of FIG. 10, seal 254 of cover 212 and seal 262 of plate 252 engage outer sides 60 of plates 252, 250 respectively. Thus, a sealing engagement is formed between cover 212 and plate 252 and between plates 252, 250. Likewise, seal 262 of plate engages upper side 42 of insulator 140 to form a sealing relationship between plate 250 and insulator 140. While regions 256, 258, 268, 270 are illustrated in FIG. 8 in a specific pattern, this is not required, and symmetric, irregular or asymmetric patterns are possible in accordance with this disclosure. Moreover, it is contemplated that greater or fewer than two regions may be formed on cover 212 and greater or fewer than three regions may be formed on lower face 74 on plates 252, 250.

Regions 256, 268, 270 cooperate with electrode sets 118, 116, and 120 respectively to enable the user to conduct multiple assays. For example, a glucose assay is conducted by partitioning a portion of sample 24 into region 268 for contact with electrode set 118, and reference electrode 122. A hematocrit assay is conducted by partitioning a portion of sample 24 into region 256 for contact with electrode set 116.

Additionally, blank current is measured by partitioning a portion of sample 24 into region 270 for contact with electrode set 120. It is contemplated that a variety of assays including those described in Table 1 can be used with sensors 210 of the present invention.

Sensor 210 is constructed in a similar manner to sensor 10, using a multi-resin injection molding. Sensor 210 is also constructed from a thermoplastic polymeric material as discussed above with reference to sensor 10. Preferably, base 12, plates 150, 152, and cover 16 are formed from a polycarbonate, hinges 23, partitions 260, and seals 253, 262 are formed of TPR.

Sensor 110 is constructed in a similar manner to sensor 10 using a multi-resin injection molding. Sensor 110 is also constructed from a thermoplastic polymeric material as discussed above with reference to sensor 10. Preferably, base 12, plates 150, 152, and cover 16 are formed from a polycarbonate, hinges 23 are constructed of a thermoplastic rubber, and partitions are formed from a TPR. When glucose, hematocrit, and blank current are to be measures, a common mediator, such as ferricyanide, is applied in liquid form to plate 252 in regions 256, 258. Discrete enzymes are applied in liquid form to plate 250 in regions 256, 288. The liquid is then evaporated, leaving the reagents in solid form coating upper face 70 and microstructures 86 of plates 250, 252. The choice of specific reagents depends on the specific analytes to be measured, and are well known to those of ordinary skill in the art.

In use, sensor 210 operates similarly to sensor 110, except that seals 254, 262 cooperate with partitions 260, 132, 134 to guide the flow of sample liquid sample 24 into regions 256, 268, 270. The glucose, hematocrit, and blank measurements are conducted as discussed above with reference to sensor 110.

Although the invention has been described in detail with reference to a preferred embodiment, variations and modifications exist within the scope and spirit of the invention as described and defined in the following claims.

What is claimed is:

1. A biosensor apparatus comprising:
   a base,
   electrodes positioned on the base,
   a cover including ports,
   at least one plate positioned between the electrodes and the cover, the at least one plate including an upper face facing the cover, a lower face, apertures, and microstructures extending from the upper face toward the cover spaced-apart from the apertures, and
   a reagent situated on the at least one plate.

2. The apparatus of claim 1, wherein the at least one plate is formed to include an upper recess defined by the upper face and a wall extending from the upper face.

3. The apparatus of claim 2, wherein the microstructures extend from the upper face into the upper recess.

4. The apparatus of claim 2, wherein the at least one plate includes a partition that extends from the upper face and divides the upper recess into regions.

5. The apparatus of claim 4, wherein the apparatus includes discrete reagents positioned in the regions.

6. The apparatus of claim 4, wherein the cover includes a seal that engages the plate when the sensor is in a folded position.

7. The apparatus of claim 2, wherein the at least one plate includes a seal that faces the base when the sensor is in a folded position.

8. The apparatus of claim 1, wherein the apparatus includes two plates positioned between the electrodes and the cover.

9. The apparatus of claim 8, wherein one plate is adjacent to the cover and the ports in the cover are in general alignment with the microstructures of the adjacent plate.

10. The apparatus of claim 9, wherein the cover and the adjacent plate cooperate to define a first distribution gap.

11. The apparatus of claim 10, wherein the adjacent plates cooperate to define a second distribution gap.

12. The apparatus of claim 1, wherein the apparatus includes three plates positioned between the electrodes and the cover.

13. The apparatus of claim 1, wherein the microstructures are cone-shaped.

14. The apparatus of claim 1, wherein the microstructures include an interrupted face.

15. The apparatus of claim 1, wherein the cover includes a seal.

16. The apparatus of claim 1, wherein the at least one plate includes a seal.

17. A biosensor apparatus comprising:
    a base,
    electrodes positioned on the base,
    a cover including ports,
    at least one plate positioned between the electrodes and the cover, the at least one plate including an upper face, a wall extending from the upper face and cooperating with the upper face to define an upper recess, apertures, and microstructures spaced-apart from the apertures and extending from the upper face into the upper recess, and the microstructures being cone-shaped, and
    a reagent situated on the at least one plate.

18. The apparatus of claim 17, wherein the microstructures include an interrupted face.

19. A biosensor apparatus comprising:
    a base,
    electrodes positioned on the base,
    a plate positioned on the base, the plate being formed to include an upper face, a lower face facing the base, first and second ends, and apertures in fluid communication with at least one of the electrodes, wherein one of the first and second ends is connected to the base,
    a cover being formed to include ports disposed through the cover, the ports being in fluid communication with the plate and offset from the apertures,
    at least one reagent positioned between the plate and the cover, and
    wherein the plate is formed to include an upper recess defined by the upper face and a wall extending from the upper face.

20. The apparatus of claim 19, wherein the plate is formed to include a lower face and a wall extending from the lower face and the lower face and the wall cooperate to define a lower recess.

21. The apparatus of claim 20, wherein the apertures extend between the upper and lower faces.

22. The apparatus of claim 21, wherein the plate includes microstructures extending from the upper face into the upper recess.

23. The apparatus of claim 19, wherein the plate includes a partition that extends from the upper face and divides the upper recess into regions.

24. A biosensor apparatus comprising:
    a base,
    electrodes positioned on the base,
    a plate positioned on the base, the plate being formed to include apertures in fluid communication with at least one of the electrodes, an upper face, a wall extending from the upper face and cooperating with the upper face to define an upper recess, a lower face, a wall extending from the lower face and cooperating with the lower face to define a lower recess, and microstructures extending from the upper face into the upper recess, wherein the apertures extend between the upper and lower faces, a cover being formed to include ports disposed through the cover, the ports being in fluid communication with the plate and offset from the apertures, and at least one reagent positioned between the plate and the cover, wherein the microstructures extend into the ports of the cover.

25. A biosensor apparatus comprising:

a base, electrodes positioned on the base, a plate positioned on the base, the plate being formed to include apertures in fluid communication with at least one of the electrodes, a cover being formed to include ports disposed through the cover, the ports being in fluid communication with the plate and offset from the apertures, at least one reagent positioned between the plate and the cover, and a hinge extending between the cover and the plate.

26. A biosensor apparatus comprising:

a base, electrodes positioned on the base, a plate positioned on the base, the plate being formed to include apertures in fluid communication with at least one of the electrodes, a cover being formed to include ports disposed through the cover, the ports being in fluid communication with the plate and offset from the apertures, at least one reagent positioned between the plate and the cover, and a hinge extending between the base and the plate.

27. A biosensor apparatus comprising:

a base, electrodes positioned on the base, a first plate positioned on the base and including an inner side facing the base, an outer side, and first and second ends, a second plate positioned on the first plate, the second plate including an inner side facing the first plate, an outer side, and first and second ends, the first and second plates each being formed to include apertures in an offset relationship relative to one another and the first ends of the first and second plates being connected, a cover positioned on the second plate, the cover being formed to include ports in an offset relationship to the apertures of the second plate, and a reagent positioned on at least one of the first and second plates.

28. A biosensor apparatus comprising:

a base, electrodes positioned on the base, a first plate positioned on the base, the first plate including microstructures extending into the apertures of the second plate, a second plate positioned on the first plate, the first and second plates each being formed to include apertures in an offset relationship relative to one another, a cover positioned on the second plate, the cover being formed to include ports in an offset relationship to the apertures of the second plate, and a reagent positioned on at least one of the first and second plates.

29. The apparatus of claim 28, wherein the second plate includes microstructures extending into the ports of the cover.

30. The apparatus of claim 29, wherein the second plate includes at least one partition extending between the microstructures and engaging the cover.

31. The apparatus of claim 28, wherein the first plate includes at least one partition extending between the microstructures and engaging the second plate.

32. A biosensor apparatus for detecting an analyte in a fluid sample, the apparatus comprising:

a base, electrodes positioned on the base, a cover spaced-apart from the electrodes and being formed to include ports sized to receive the fluid sample a reagent, and means for distributing the fluid sample and the reagent from the ports in the cover to the electrodes, the distributing means being formed to spread the fluid sample radially outwardly from the port in the cover and to also permit the fluid to flow in a direction generally perpendicular to the cover toward the electrodes, wherein the distributing means comprises an upper face facing the cover, a lower face, and microstructures extending from the upper face toward the cover.

33. The apparatus of claim 32, wherein the distributing means includes perforated plates positioned between the cover and the base.

34. The apparatus of claim 33, wherein the distributing means includes two perforated plates.

35. The apparatus of claim 33, wherein the distributing means includes three perforated plates.

* * * * *